(12) United States Patent
Milosevic et al.

(10) Patent No.: US 7,671,985 B1
(45) Date of Patent: Mar. 2, 2010

(54) DEVICE FOR SMALL SPOT ANALYSIS USING FIBER OPTIC INTERFACED SPECTROMETERS

(76) Inventors: Milan Milosevic, 9 Janson Dr., Westport, CT (US) 06880; Violet Milosevic, 9 Janson Dr., Westport, CT (US) 06880

( * ) Notice: Subject to any disclaimer, the term of this patent is extended or adjusted under 35 U.S.C. 154(b) by 375 days.

(21) Appl. No.: 11/716,775

(22) Filed: Mar. 12, 2007

Related U.S. Application Data

(60) Provisional application No. 60/781,767, filed on Mar. 13, 2006.

(51) Int. Cl.
*G01J 3/28* (2006.01)

(52) U.S. Cl. .......................... 356/326; 356/301; 356/73

(58) Field of Classification Search .................. 356/73, 356/326, 301, 317, 318
See application file for complete search history.

(56) References Cited

U.S. PATENT DOCUMENTS

| | | | | |
|---|---|---|---|---|
| 4,716,293 A | * | 12/1987 | Harrick | ....................... 250/340 |
| 4,859,064 A | * | 8/1989 | Messerschmidt et al. | .... 356/446 |
| 5,088,821 A | | 2/1992 | Milosevic | |
| 5,659,397 A | * | 8/1997 | Miller et al. | ................ 356/446 |
| 5,818,996 A | | 10/1998 | Doyle | |
| 5,842,995 A | * | 12/1998 | Mahadevan-Jansen et al. | .......................... 600/473 |
| 6,181,427 B1 | | 1/2001 | Yarussi et al. | |
| 6,571,118 B1 | | 5/2003 | Utzinger et al. | |
| 6,765,668 B2 | * | 7/2004 | Gardner et al. | .............. 356/301 |
| 6,819,411 B1 | * | 11/2004 | Sharpe et al. | ................. 356/72 |
| 7,148,963 B2 | * | 12/2006 | Owen et al. | ................. 356/301 |

OTHER PUBLICATIONS

M. Milosevic and V. Milosevic, "The Video Barrelino", Proc. IRUG6, 284-287, 2004).

* cited by examiner

*Primary Examiner*—L. G Lauchman

(57) ABSTRACT

The present invention is an optical device for small spot analysis by diffuse reflectance using fiber optic interfaced spectrometers. The device comprises a source of electromagnetic radiation and a set of mirrors designed to project most of the radiation from the said source onto a less than 1 mm diameter spot on the sample, collect a portion of the radiation reflected by the sample and refocus this reflected radiation into an optical fiber. The said optical fiber then brings the said reflected radiation into a fiber optic interfaced spectrometer for spectral analysis. A means for the magnified viewing of the sample and the precise selection of the sampling spot for analysis is integrated into the invented device. Adding a digital camera and a laser module to the said device enables nearly simultaneous multimodal analysis of the same sampling spot by diffuse reflectance, Raman, and fluorescence spectroscopy and by image analysis.

7 Claims, 2 Drawing Sheets

DEVICE FOR SMALL SPOT ANALYSIS USING FIBER OPTIC INTERFACED SPECTROMETERS

CROSS-REFERENCE TO RELATED APPLICATIONS

This application claims the benefit of provisional patent application Ser. No. 60/781,767, filed 2006 Mar. 13 by the present inventors.

FEDERALLY SPONSORED RESEARCH

Not Applicable

SEQUENCE LISTING OR PROGRAM

Not Applicable

BACKGROUND

1. Field of Invention

The field of the present invention relates to the multimodal analysis of a small spot on a sample by spectroscopy and sample image analysis. Specifically, it relates to the spectroscopic analysis of the sample using a fiber optic interfaced spectrometer.

2. Prior Art

There has always been an impetus to build spectrometric equipment that would bring radiation to the sample outside the sample compartment of a spectrometer. Dedicated analyzers were and still are being developed that integrate the functions of a spectrometer and a probe in a single package, for example U.S. Pat. No. 6,181,427 B1 (2001) issued to Yarussi, and U.S. Pat. No. 5,659,397A (1997) issued to Miller.

Recent advances in opto-electronics enabled the construction of small hand held full-featured UV-VIS-NIR spectrometers that spectrally analyze radiation brought in by standard fiber optics cables. Two types of fiber optic diffuse reflectance probes exist for use with fiber optic spectrometers: wand like fiber optic probes and integrating spheres.

The most common method for making the wand like fiber optics probes is to use one or more fibers in a bundle to bring light to the sample. The reflected light is collected by other fibers in the bundle and returned to the spectrometer for analysis.

A huge variety of different probes of this general type exists. The basic parameters, such as the number of fibers used to bring light to the sample, the number and position of fibers used to collect the reflected light, fiber packing, diameters, positions, end shapes, are all varied in order to optimize a particular aspect of the analysis. An example is described in U.S. Pat. No. 6,571,118 B1 (2003) issued to Utzinger. These wand-like probes are relatively simple and generally don't require any mirrors. Another variation of the wand like probes that uses light guides and lenses for the interface with a sample is described in U.S. Pat. No. 5,818,996 (1998) issued to Doyle.

The shortcomings of wand like probes are that they obscure the exact sampling spot. This makes sampling spot selection difficult and hence the precise position of the sampled area is somewhat uncertain. Another shortcoming of these probes is that they are subject to a numerical aperture restriction due to optical fibers that limits the amount of light that can be carried to and from the sample. Also, their spectral range is limited by the fibers used.

Wand-like fiber optics probes work well for certain applications and for spectral regions for which suitable optical fibers exist, such as the visible and near infrared spectral regions. In the infrared region no such fibers exist and, in some extreme cases, such as U.S. Pat. No. 5,088,821 (1992) issued to Milosevic, elaborate light pipe systems were built to bring light to sampling stations several meters away from the spectrometer. Several of the sampling stations had integral detectors and returned the electrical signal back to the spectrometer.

Fiber optics limits the numerical aperture of the light that it carries. Only the portion of the diffusely reflected light that can be carried by a fiber back to the spectrometer can be utilized for detection. Following the concept disclosed in U.S. Pat. No. 5,088,821 (1992) issued to Milosevic, one diffuse reflectance probe (M. Milosevic and V. Milosevic, "The Video Barrelino", Proc. IRUG6, 284-287, 2004) sought to overcome this limitation by incorporating the detector directly into the probe. An integral detector eliminates the need to return the diffusely reflected light back to the spectrometer. By eliminating the need to carry the light to the detector via an optical fiber a much larger amount of diffusely reflected light could be brought to the detector. However, this probe is not usable with fiber optics spectrometers since it returns an electrical signal, not radiation, back to the spectrometer.

Diffuse reflection probes, based on the well known integrating sphere concept, were developed for use with fiber optics spectrometers and are commercially available. Some of these probes employ an integrated radiation source to illuminate the sample. The reflected radiation is returned via fiber optics back to the spectrometer. These probes are made for a very specific purpose. They are constructed to enable the measurement of the total reflectance of a diffusely reflecting sample. They analyze large sample spots—typically around 25 mm in diameter. They provide spatially and directionally uniform irradiation of the sampling area, and are designed to integrate the reflectance from large uneven samples where local unevenness is not of interest and the average value of the reflectance is all that matters. Samples such as grain are analyzed for water, fat, fiber, protein, etc. content since grain to grain variation is not important. Smaller spots can generally be analyzed by aperturing the sampled area. This sample size reduction however is achieved at the expense of the amount of radiation collected from the sample. These probes are thus not adequate for use with small (less than 1 mm in diameter) sample spots.

SUMMARY

The present invention is a diffuse reflection device for use with fiber optic interfaced spectrometers. It comprises an axially symmetric ellipsoid chamber having a highly reflective interior surface, a source of electromagnetic radiation and a 900 off-axis ellipsoid collection mirror. The radiation source is placed in a focal point of the ellipsoid chamber mirror.

When a sample is placed in the ellipsoid chamber mirror's other focal point, most of the radiation from the radiation source is refocused by the ellipsoid chamber mirror into a small spot (~1 mm diameter) on the sample where it is diffusely reflected. The diffusely reflected radiation is collected and brought into an entrance aperture of an optical fiber by the ellipsoid collection mirror. This is done by placing the collection mirror inside the chamber mirror so that one of its focal points is on the sample and its other focal point on the entrance aperture of the optical fiber connected to a spectrometer. The portion of the radiation reflected off the sample that can be brought back to the spectrometer for analysis is limited by the numerical aperture of the fiber. Thus the collection mirror used to image the reflected radiation onto the optical fiber is sized to match the numerical aperture of the fiber. The entire remaining space above the sample not used by the collecting optics is utilized to bring incident radiation onto the sample thus maximizing the radiation energy brought to the spectrometer.

The area immediately above the sample is left unobstructed thus allowing the possibility of viewing of the sample. A lens can be incorporated into a cover placed over the top of the ellipsoid chamber mirror to enable the magnified viewing of the sample and the precise selection of the sampling spot. Alternatively, a lens may be used to form an image of the sample on a sensor of a digital camera. This enables the viewing of the sample on an LCD or CRT display as well as image capture for image analysis and storage.

A lower protective cover with an opening in the center may be placed under the ellipsoid chamber mirror. The thickness of the said cover could be such that its bottom surface is in the sampling plane. In this way when the device is rested on the sample the sample is in the proper position for analysis. The size of the said opening is such to permit unobstructed illumination of the sampling spot. Additionally, an optically transparent window can be placed to cover the said opening. Some alternatives for the shape of this window are a flat disc, hemispherical shell or a solid hemisphere. The solid hemisphere option is particularly useful for the diffuse reflectance analysis of opaque liquids and pastes. When the refractive indices of the said hemisphere and the liquid or paste sample are matched, the reflection at the sample hemisphere interface is suppressed. Thus the transfer of radiation into the sample is maximized.

The radiation source can be powered by a battery pack, an external power source or through a computer.

Instead of bringing the collected diffusely reflected radiation to the spectrometer via an optical fiber, the entrance port of the spectrometer could be coupled directly to the diffuse reflectance device described herein.

The device described herein may be embodied in a portable device containing the device of the present invention, a portable spectrometer, and a portable computer.

The diffuse reflectance device described herein possesses the necessary collection optics to collect radiation reflected from a small area of a sample and input it into a spectrometer via an optical fiber. Thus, this device is also optimized to collect forms of radiation other than diffusely reflected radiation. If the sample is illuminated by laser light, it could emit fluorescent light, or the laser light could be Raman scattered by the sample. This secondary radiation can then be collected by the collecting mirror and imaged into the optical fiber. Just as with the diffusely reflected light, as much of this light that can be carried by an optical fiber to the spectrometer is collected. The spectral analyses of Raman and fluorescent radiations (Raman spectroscopy and fluorescence spectroscopy) are common analytical techniques. They are also complementary techniques to diffuse reflection spectroscopy. The information they provide about the sample is of a different nature and in addition to what is provided by diffuse reflection spectroscopy. Thus, by adding a laser source, the present invention is enhanced to provide additional types of spectroscopic analyses and hence a more complete analysis of a sample.

DRAWINGS

Figures

Figure 1:
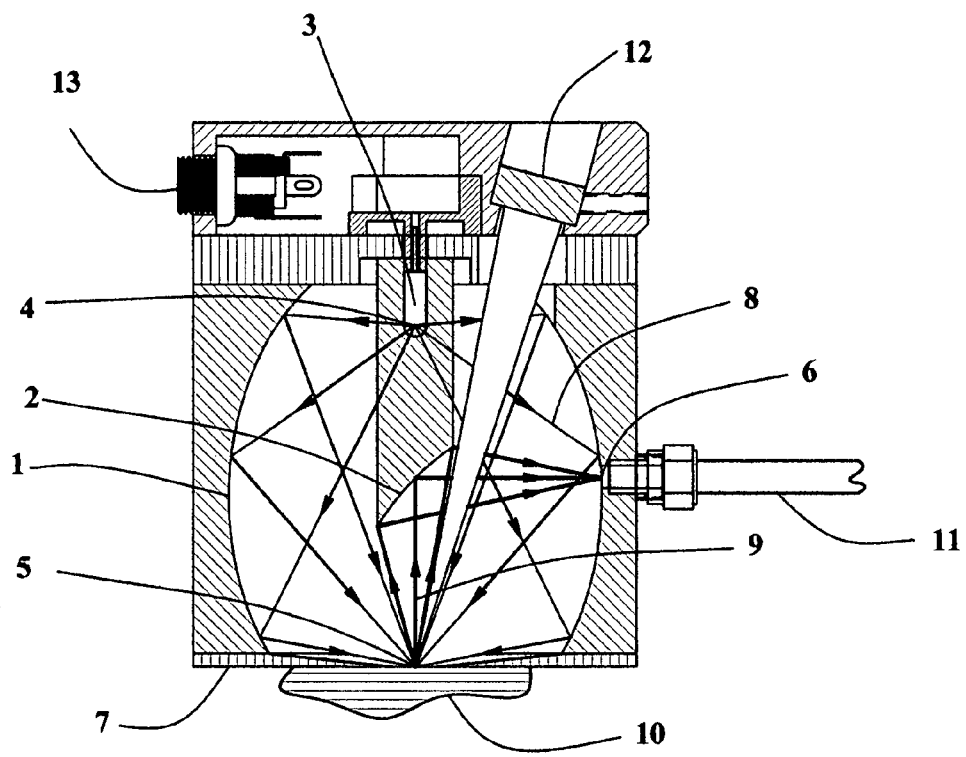
FIG. 1 is a side elevational view of an embodiment of the present invention in which sample viewing is through a magnifying glass.

REFERENCE NUMERALS 1 axially symmetric ellipsoid mirror
2 collecting ellipsoid mirror
3 source of electromagnetic radiation
4 one focal point of the axially symmetric ellipsoid mirror 1
5 sampling spot
6 entrance face of the optical fiber 11
7 bottom cover
8 incoming light ray
9 diffusely reflected light ray
10 sample
11 optical fiber
12 lens
13 connector
14 optics
15 image plane
16 optical sensor of a digital camera
17 thin flat disc
18 hemispherical shell
19 solid hemisphere
20 laser source
21 monochromatic light beam
22 Raman or fluorescence radiation

DETAILED DESCRIPTION OF THE PREFERRED EMBODIMENTS

FIG. 1 illustrates one embodiment of the present invention. A source of electromagnetic radiation 3 (light bulb, LED, etc) is placed into one focal point 4 of the axially symmetric ellipsoid mirror 1. By the well-known property of ellipsoid mirrors, all light coming from one focal point of the mirror is relayed to the other focal point. This second focal point becomes the sampling spot 5 where a sample 10, having a diffusely reflecting surface, is introduced for measurement. A cover 7 could be placed on the bottom of the ellipsoid mirror 1 with a thickness such that the sampling spot 5 is in its lower surface. The cover 7 has an opening centered on the sampling spot 5 and of a size sufficient to allow the unobstructed illumination of the sample.

By resting the device on the flat sample 10 the surface of the sample is just in the right position for analysis. Incoming light exemplified by ray 8 reflects off the sample diffusely i.e. the angle at which the incoming ray of light strikes the sample does not determine the angle at which the said ray is reflected off the sample. Because of this, the diffusely reflected light fills the entire space above the sample. A portion of diffusely reflected light exemplified by ray 9 is imaged by the collecting ellipsoid mirror 2 onto the entrance face 6 of the optical fiber 11. The said optical fiber 11 carries the reflected light to the spectrometer for analysis.

In the embodiment shown in FIG. 1 a lens 12 is used as a magnifying glass allowing the direct magnified viewing of the sample. Light source 3 used for the diffuse reflectance analysis of the sample is simultaneously used to illuminate the sample for viewing. Connector 13 provides power to light source 3.

Figure 2:
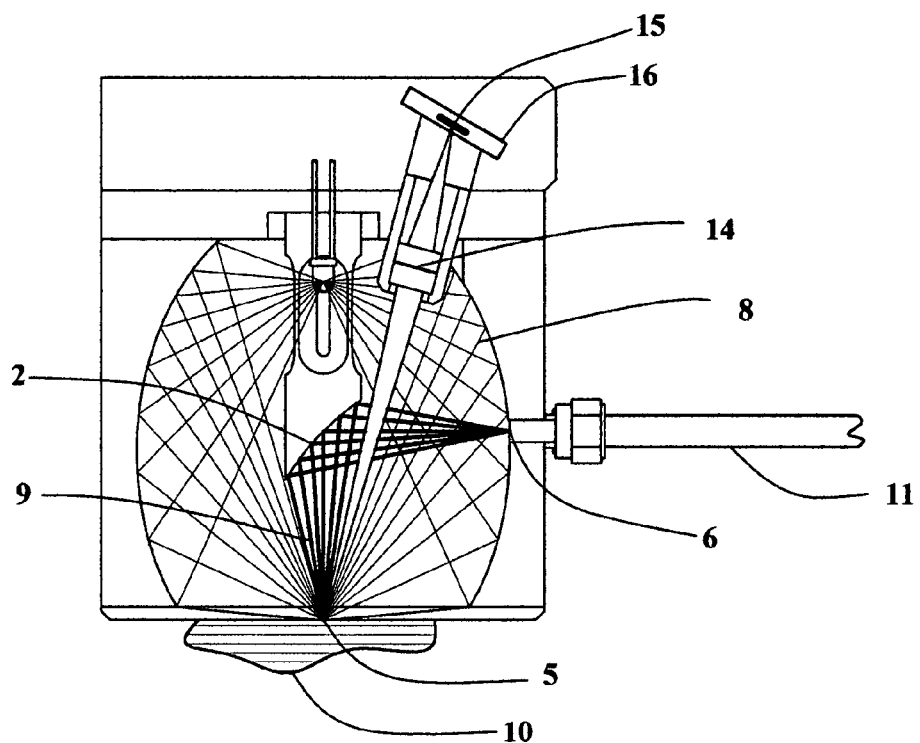
FIG. 2 is a side elevational view of an embodiment of the present invention in which sample viewing is by means of a digital camera.

A different choice of optics 14 could be utilized to image the sample spot 5 into the image plane 15 as shown in FIG. 2. An optical sensor of a digital camera 16 could then be placed into the said image plane 15 and a live image of the sample spot could be displayed on an image-displaying device such as a CRT monitor or an LCD.

It can be seen from FIG. 2 that the incident light 8 fills the entire space above the sampling spot 5 except for the portion of the solid angle used to collect the reflected light 9 shown by heavier lines. The size of the collecting mirror 2 is chosen just large enough to produce radiation with a numerical aperture matching that of the optical fiber 11. The shape of the collecting mirror 2 is chosen such that it images the sample spot 5 onto the entrance face 6 of the fiber 11 in a 1:1 fashion. Because of the 1:1 imaging, the size of the area on the sample that is analyzed is the same as the size of the entrance aperture of the optical fiber used—generally under 1 mm in diameter.

Figure 3:
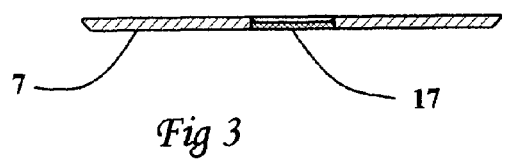
FIG. 3 is a side elevational view of the lower cover with a disc shaped window.

The opening on the bottom cover 7 could be left open, or it could be closed by an optically transparent window to protect the optics inside the device from the exterior. This window could be in the shape of a thin flat disc 17 imbedded into the cover as shown in FIG. 3.

Figures 4, 5:
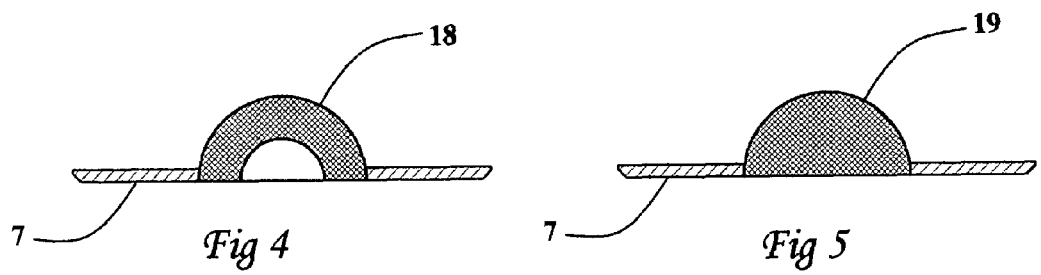
FIG. 4 is a side elevational view of the lower cover with a hemispherical shell window.
FIG. 5 is a side elevational view of the lower cover with a solid hemispherical window.

Alternatively, the window can be made in the shape of a hemispherical shell 18 centered on the sampling spot, as shown in FIG. 4.

Another variation would be a solid hemisphere 19 made of a transparent material of substantially the same refractive index as that of the sample centered on the sampling spot as shown in FIG. 5.

Figure 6:
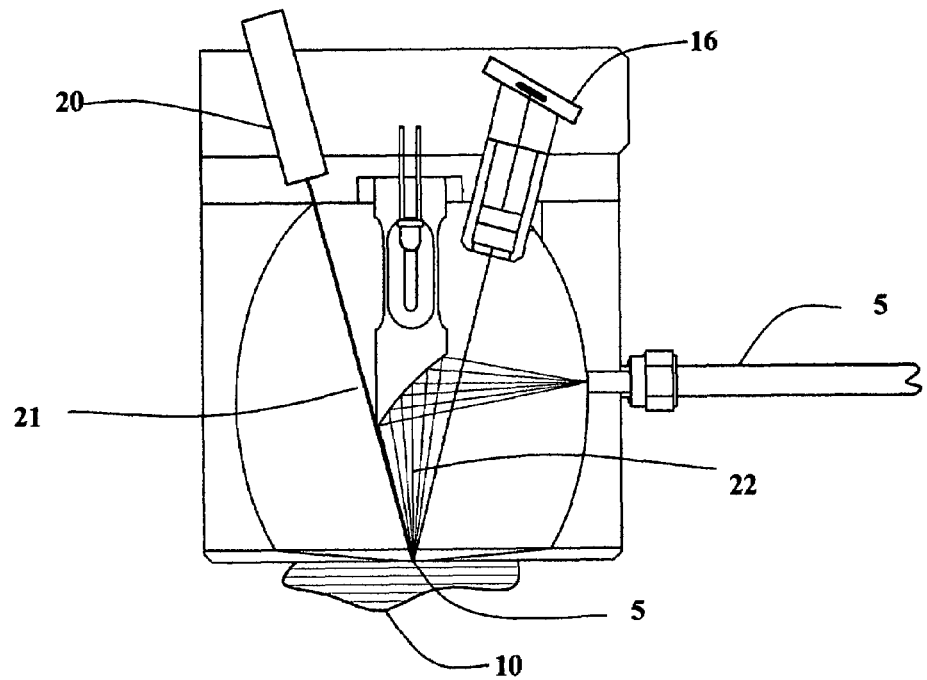
FIG. 6 is a side elevational view of an embodiment of the present invention showing its use for Raman and/or fluorescence spectroscopy.

In FIG. 6 a laser source 20 is shown aimed at the sampling spot 5 projecting a monochromatic light beam 21 capable of exciting either Raman scattering or fluorescence by the sample 10. The Raman or fluorescence radiation 22 emitted by the sample is collected and sent to a spectrometer in the same way as is the diffusely reflected radiation. The installation of laser module 20 should be quick and simple so that lasers emitting different wavelengths can be easily exchanged to facilitate the selection of the optimum exciting wavelength for a specific application.

The embodiment shown in FIG. 6 illustrates how the device of the present invention can be used as a multimodal analyzer when connected to a spectrometer and computer. The sample is placed in spot 5. The precise selection of the sampling spot of interest is achieved by observing a live image taken by the digital camera 16 on a computer monitor. The image of the selected spot is captured for image analysis and future reference. Simultaneously a diffuse reflectance spectrum of the same spot on the sample can be acquired. The light source 3 is switched off and laser 20 is switched on enabling the excitation of Raman and/or fluorescence radiation of the same spot on the sample. Raman/fluorescence spectra can now be acquired. Thus up to four different analyses of the same spot on the sample can be performed almost simultaneously. This is the consequence of the unique optical design that leaves the space above the sampling spot unobstructed.

The above embodiments are given as illustrative examples and are not intended to impose any limitations on the invention. It will be readily appreciated that many deviations may be made from the specific embodiments disclosed in this specification without departing from the invention. Accordingly, it is intended to cover all such modifications as within the scope of this invention.

We claim:

1. A device for small spot analysis by diffuse reflection spectroscopy using fiber optic interfaced spectrometers comprising:
   a) an internal radiation source, said radiation diverging from said source into substantially all directions,
   b) an axially symmetric ellipsoid chamber mirror having two segments near the poles cut away perpendicular to the axis of said chamber mirror so that one focal point of said chamber mirror is near the upper cutout but still inside the space enclosed by the surface of said chamber mirror while the other focal point is near the lower cutout and protruding slightly outside said chamber mirror and said chamber mirror having a small hole drilled near the equator of said chamber mirror perpendicular to said axis, the first focal point containing said source so that by the property of ellipsoid mirrors most of said radiation emitted by said source is refocused into the second focal point within a spot less than 1 mm in diameter, said second focal point being the sampling spot wherein a sample is introduced for analysis,
   c) an ellipsoid collecting mirror shaped as a segment of a 90° off-axis ellipsoid positioned inside said chamber mirror above said sampling spot so that one focal point of said collecting mirror coincides with said sampling spot and the other focal point coincides with said hole in said chamber mirror so that radiation diffusely reflected from said sample in the first focal point of said collecting mirror is, by the property of ellipsoid mirrors, refocused into the second focal point of said collecting mirror and can escape outside said chamber mirror through said hole,
   d) a fiber optics interfaced spectrometer placed outside said chamber mirror having an entrance slit positioned near said hole and in position to receive said diffusely reflected radiation from said collecting mirror either directly or relayed through an optical fiber from the second focal point of said collecting mirror to said entrance slit of said spectrometer to spectrally analyze said diffusely reflected radiation.

2. The device from claim 1 further including an upper cover attached to the upper side of said chamber mirror providing a cover over the interior of said chamber mirror and a frame to which other elements can be attached.

3. The device from claim 2 further comprising a magnifying glass, imbedded into said upper cover, whereby enabling the direct viewing of the sample to facilitate visual selection of said sampling spot, said sampling spot being illuminated and delineated by said source for viewing through said magnifying glass.

4. The device from claim 2 further comprising a digital camera, attached to said upper cover, aimed at said sampling spot and an LCD attached to said device, whereby said digital camera and said LCD jointly providing live image display and capture of said sampling spot and also enabling the visual selection of said sampling spot for analysis by diffuse reflection spectroscopy.

5. The device from claim 2 further comprising a laser light source, attached to said upper cover, aimed at said sampling spot, whereby said laser enabling that the sample be analyzed by Raman and fluorescence spectroscopy in addition to diffuse reflection spectroscopy.

6. The device from claim 3 further comprising a laser light source, attached to said upper cover, aimed at said sampling spot, whereby said laser enabling that the sample be analyzed by Raman and fluorescence spectroscopy in addition to diffuse reflection spectroscopy.

7. The device from claim 4 further comprising a laser light source, attached to said upper cover, aimed at said sampling spot, whereby said laser enabling that the sample be analyzed by Raman and fluorescence spectroscopy in addition to diffuse reflection spectroscopy.

* * * * *